United States Patent [19]

Holan et al.

[11] 4,391,820
[45] Jul. 5, 1983

[54] INSECTICIDAL ESTER ENANTIOMERS

[75] Inventors: George Holan, Brighton; Reimund Walser, Box Hill, both of Australia

[73] Assignee: Commonwealth Scientific and Industrial Research Organization, Australia

[21] Appl. No.: 269,735

[22] Filed: Jun. 2, 1981

[30] Foreign Application Priority Data

Jun. 13, 1980 [AU] Australia .................. PE4038/80

[51] Int. Cl.³ .................. A01N 43/16; C07C 69/76; A01N 37/10
[52] U.S. Cl. .................. 424/282; 560/59; 560/102; 424/308
[58] Field of Search .................. 560/59, 102; 424/308, 424/282

[56] References Cited

U.S. PATENT DOCUMENTS

| | | |
|---|---|---|
| 3,657,317 | 4/1972 | Coffee . |
| 3,968,137 | 7/1976 | Andreades et al. . |
| 4,130,656 | 12/1978 | Greuter et al. .................. 424/304 |
| 4,235,926 | 11/1980 | Holan et al. .................. 424/282 |

FOREIGN PATENT DOCUMENTS

249037  5/1947  Switzerland .

OTHER PUBLICATIONS

Elliott et al., Nature, (London), vol. 243, p. 710, (1973).

Primary Examiner—Ethel G. Love
Attorney, Agent, or Firm—Bacon & Thomas

[57] ABSTRACT

The (−) (−) diastereoisomers of the α-cyano-3-phenoxybenzyl and α-ethynyl-3-phenoxybenzyl esters of 1-(4-ethoxyphenyl)-, 1-(4-chlorophenyl)-, and 1-(3,4-methylenedioxyphenyl)-2,2,3,3-tetrafluorocyclobutane carboxylic acid.

9 Claims, No Drawings

INSECTICIDAL ESTER ENANTIOMERS

This invention relates to new insecticidal compounds, methods of preparing these compounds and to new insecticidal compositions containing the compounds.

Throughout this specification, where the context permits, the word "insect" is used in its broad common usage and includes spiders, mites, nematodes and other pests which are not classed as insects in the strict biological sense. Thus the term implies reference not only to those small invertebrate animals belonging mostly to the class Insecta, comprising six-legged, usually winged forms, such as beetles, bugs, flies and the like, but also to other allied classes of arthropods whose members are wingless and usually have more than six legs, such as spiders, wood lice and the like, and especially to the order Acaridae which includes the mites and ticks. The words "insecticide" and "insecticidal" are similarly used.

The compounds provided by this invention fall within the broad class of compounds disclosed in our copending Australian Patent Application No. 42723/78. Such compounds have the general formula I

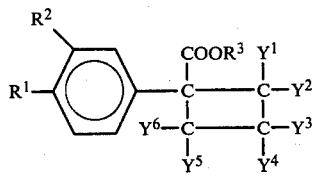

wherein $R^1$ is hydrogen or a methoxy, ethoxy, propoxy, butoxy, tetrafluoroethoxy, methylthio, ethylthio, propylthio, fluoro, chloro, bromo, methyl, ethyl, or nitro group, and $R^2$ is hydrogen or a methyl group, or $R^1$ and $R^2$ together form a methylenedioxy group;

$R^3$ is hydrogen, or a lower alkyl group, or one of the following groups (a) to (f):

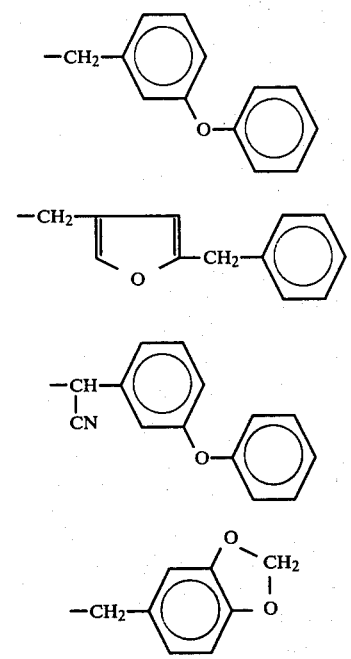

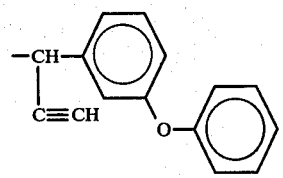

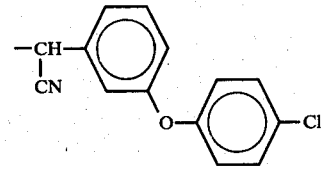

and $Y^1$, $Y^2$, $Y^3$, $Y^4$, $Y^5$ and $Y^6$ are the same or different groups and each is hydrogen or a fluoro, bromo or chloro group, with the proviso that when $R^1$ is fluoro, chloro, bromo or methyl and $R^2$ is hydrogen, then one of $Y^1$ to $Y^6$ is other than hydrogen.

As described in our aforementioned copending application, the compounds of formula I in which $R^3$ is one of groups (a) to (f) are active as insecticides, having an insecticidal activity an order of magnitude greater than most known insecticides. The compounds also possess the property of contact repellency to insects.

As also mentioned in our copending Application, the compounds of the formula I above are optically active, the acids (formula I, $R^3$=H) having an assymetric carbon atom ($C_1$ of the cyclobutane ring) and thus are potentially resolvable into optical isomers.

Thus the acid, 1-(4-ethoxyphenyl)-2,2,3,3-tetrafluorocyclobutane carboxylic acid (formula I, $R^1$=OEt, $R^2$=$R^3$=H, $Y^1$ to $Y^4$=F; $Y^5$, $Y^6$=H) was resolved and esterified with 3-phenoxybenzyl alcohol to give the R(−) isomer of the ester (formula I, $R^1$=OEt, $R^2$=H, $R^3$=(a), $Y^1$ to $Y^4$=F; $Y^5$, $Y^6$=H). The latter was shown to have more than twice the activity of the racemic form of the ester.

Where the alcohol ($R^3OH$), from which the esters are derived, also has an assymetric centre, as in the case where $R^3$ is of the groups (c), (e) or (f), the esters are capable of existing in four enantiomeric forms as well as the racemic forms.

We have now investigated these enantiomeric forms and have found that they show surprising differences in insecticidal activity. In general, we have found that of the four possible enantiomers, one is highly active, while the others are of low activity. Usually, the level of activity of the most active enantiomer is considerably greater, when compared with the activity of the unresolved compound, than would be expected if in the unresolved compound, the lower activity enantiomers were acting simply as inert diluent. In other words, the low activity enantiomers appear to have an inhibitory or antagonistic action on the most active enantioner.

Accordingly, the present invention provides the (−)(−) diastereoisomers of the compounds of the formula I stated above wherein $R^1$ is ethoxy or chloro and $R^2$ is hydrogen; or $R^1$ and $R^2$ together form a methylenedioxy group; $R^3$ is one of the groups (c) and (e); each of $Y^1$ to $Y^4$ is fluoro; and $Y^5$ and $Y^6$ are hydrogen. The configurations of the acid and alcohol moieties are as measured by optical rotation.

The preferred compounds provided by this invention are:

(−)(−)-α-cyano-3'-phenoxybenzyl 1-(4-ethoxyphenyl)-2,2,3,3-tetrafluorocyclobutane carboxylate;

(−)(−)-α-ethynyl-3'-phenoxybenzyl 1-(4-ethoxyphenyl)-2,2,3,3-tetrafluorocyclobutane carboxylate;

(−)(−)-α-ethynyl-3'-phenoxybenzyl 1-(4-chlorophenyl)-2,2,3,3-tetrafluorocyclobutane carboxylate;

(−)(−)-α-ethynyl-3'-phenoxybenzyl 1-(3,4-methylenedioxyphenyl)-2,2,3,3-tetrafluorocyclobutane carboxylate.

The general methods of preparation of the acids and esters of formula I are described in our aforesaid copending application. Briefly stated the compounds I in which R is one of the groups (a) to (f) may be prepared by esterification of the free acid (formula I, $R^3$=H) with the appropriate alcohol $R^3$OH, where $R^3$ is one of the groups (a) to (f). Such esterification may be carried out by any suitable known method, e.g., by direct reaction, or by prior conversion of the acid and/or the alcohol to a suitable reactive derivative, or by an ester interchange reaction between the alcohol $R^3$OH ($R^3$=(a) to (f)) and a lower alkyl ester of the acid.

The specified diastereoisomers of the present invention may be prepared by first resolving the appropriate acid (formula I, $R^3$=H) and/or the alcohol ($R^3$OH; $R^3$=(c) or (e)) to obtain the (−) forms of the acid and-/or the alcohol, and forming the ester by the general method just stated, under conditions which do not racemize the resolved component. Where the acid or alcohol is unresolved before esterification, the individual ester diastereoisomers are separated, after esterification by a suitable method.

Any suitable method can be used for resolution of the starting materials. In the case of the acid we have obtained good results by forming the amide with (−)-α-phenylethylamine, separating the respective diastereoisomers by liquid chromatography and hydrolysing the separated isomers under mild (non-racemizing) conditions.

Separation of the ester enantiomers, where necessary, after esterification can be obtained by preparative liquid chromatography (HPLC).

The compounds of the invention show insecticidal activities which are superior to the unresolved enantiomer mixtures. When used with potentiators (as described hereinafter) their activities are still further enhanced—to as much as 10 times the potentiated activity of the next best enantiomer mixture.

The new compounds also show potentiated activity which is superior to known commercial insecticides of the synthetic pyrethroid type.

The new compounds described herein may be dissolved in a suitable organic solvent, or mixture of solvents, to form solutions or brought into aqueous suspension by dispersing organic solvent solutions of the compounds in water, to provide useful liquid compositions, which may be incorporated, for example, into aerosol-type dispersions with the usual propellants.

The compounds may also be incorporated in solid compositions which may include inert solid diluents or carriers, to form useful solid compositions. Such compositions may also include other substances such as wetting, dispersing or sticking agents, and may be prepared in granular or other forms to provide slow release of the compounds over an extended period of time. The compounds may be employed in such compositions either as the sole toxic agent or in combination with other insecticides such as pyrethrum, rotenone, or with fungicidal or bactericidal agents, to provide compositions useful for household and agricultural dusts and sprays, textile coating and impregnation, and the like.

In particular, the compounds of the invention may be advantageously combined with other substances which have a synergistic or potentiating action. Generally such substances are of the class of microsomal oxidase inhibitors i.e., they inhibit the detoxification of insecticides in insects produced by the action of oxidative enzymes. Typical substances of this type are the pyrethrin synergists of which the following are examples:

| Common Name | Chemical Name |
|---|---|
| Piperonyl butoxide | α[2-(2-butoxyethoxy)ethoxy]-4,5-methylenedioxy-2-propyltoluene |
| Piperonyl cyclonene | 3-hexyl-5(3,4-methylenedioxyphenyl)-2-cyclohexanone |
| "Sesoxane" (Sesamex) | 2-(3,4-methylenedioxy-phenoxy)-3,6,9-trioxaudecane |
| "Sulfoxide" | 1,2-(methylenedioxy)-4-[2-(octylsulfinyl)propyl]-benzene |
| n-Propyl isome | dipropyl-5,6,7,8-tetrahydro-7-methylnaphtho-[2,3-d]-], 3-dioxole-5,6-dicarboxylate |

("Sesoxane", "Sesamex" and "Sulfoxide" are Registered Trade Marks).

Piperonyl butoxide is particularly useful as a potentiator. The amount of piperonyl butoxide used may vary from 1/1000th to five times the weight of the compound I the preferred range being from about 1/100th to an equal part by weight. 'Sesoxane' (made by Shulton Inc., Clifton, N.J. U.S.A.) also is a useful potentiator in similar amounts.

The preparation and properties of the compounds of the invention are illustrated by the following specific examples. It should be noted, of course, that these examples are intended to be illustrative of the methods and procedures utilized in preparing the compounds and that they are not intended to be restrictive or to be regarded as embodying the only way in which the compounds can be formed and recovered.

EXAMPLE 1

Preparation of Racemic
1-(4-ethoxyphenyl)-2,2,3,3-tetrafluorocyclobutane carboxylic acid (a) 2-(4-ethoxyphenyl)propenoic acid ethyl ester Alcohol-free sodium ethoxide freshly prepared from sodium (13.9 g) and excess ethanol was slurried in dry benzene (200 ml.). To this suspension diethyl oxalate (88.5 g) was added over 15 minutes. Ethyl-p-ethoxyphenylacetate (114.2 g) was added to the resulting clear yellow solution over 30 minutes at room temperature. After a further 1 hour period the reaction mixture solidified. The solid product, sodium diethyl-2-p-ethoxyphenyl-3-ethoxy-3-oxido-oxaloacetate was triturated and washed well with ether. The combined ether washings were evaporated to a small volume to obtain a second crop of the salt.

The combined yield was 227.4 g.

The sodium salt was acidified by adding it in portions to a well stirred emulsion of equal parts of diethyl ether and dilute acetic acid (approximately 10%). After separation the ether layer was washed with water and dilute sodium bicarbonate solution, and dried with anhydrous sodium sulphate. After evaporation of the ether, the resulting oil was crystallized from petroleum ether (b.p.

60°–80°), to yield diethyl 2-p-ethoxyphenyloxaloacetate 143.8 g (85%), m.p. 59°–60°.

The keto-ester thus obtained (143.8 g) was stirred in dilute formaldehyde solution (62 ml 37% formaldehyde + water 220 ml) and to the suspension potassium carbonate solution (54.5 g, in water 280 ml) was added dropwise. At the end of the addition, ether was added to the stirred suspension to dissolve the gummy precipitate which formed and after an additional 15 minutes, gas evolution commenced. When this gas evolution ceased (after about 2 hours) the reaction mixture was extracted with additional ether and the combined ether extracts were washed with water and evaporated after drying with $Na_2SO_4$. The yield of ethyl 2-(4-ethoxyphenyl) propenoate (isolated as a yellow oil) was 97.8 g (79.8%).

(b) Ethyl 1-(4-ethoxyphenyl)-2,2,3,3-tetrafluorocyclobutane carboxylate 2-(4-ethoxyphenyl)propenoic acid ethyl ester (13.2 g) was mixed with benzene (7.5 ml), α-pinene (2 drops) N-ethyldiisopropyl amine (2 drops) and tetrafluoroethylene (15.5 ml) and heated to 150°–155° for 24 hours then 155°–60° C. for 17 hours. After evaporation of volatile materials the residue (16.6 g) was dissolved in dichloromethane and chromatographed on a column of silica gel to give the ester as a colourless oil 14.5 g (75%). Analysis: C 56.47%, H 5.24%, F 23.4%, $C_{15}H_{16}F_4O_3$ requires C 56.25%, H 5.04%, F. 23.7%.

(c) 1-(4-ethoxyphenyl)-2,2,3,3-tetrafluorocyclobutane carboxylic acid

Ethyl 1-(4-ethoxyphenyl)-2,2,3,3-tetrafluorocyclobutane carboxylate (14.5 g) was dissolved in ethanol (100 ml) and a 10% w/w solution of sodium hydroxide in water (100 ml) was added and the mixture refluxed for 2.5 hours. The mixture was cooled, added to ice water and extracted with diethyl ether. The aqueous layer was acidified and the precipitate was filtered off, washed with water, dried and crystallised from 60°–80° petroleum ether to give the acid mp 112°–3° C. Yield 11.2 g (85%). Analysis: C 53.20% H 4.22%, F 25.9%. $C_{13}H_{12}F_4O_3$ requires C 53.43%, H 4.14%, F 26.0%.

EXAMPLE 2

Resolution of 1-(4-ethoxyphenyl)-2,2,3,3-tetrafluorocyclobutane Carboxylic Acid (a) Formation and Resolution of diastereoisomeric amides 1-(4-Ethoxyphenyl)-2,2,3,3-tetrafluorocyclobutane carboxylic acid (5.84 g) was converted to the acid chloride by heating on a steam bath with an excess of thionyl chloride (4.76 g). After the evaporation of excess $SOCl_2$, the acid chloride, without further purification, was reacted in benzene (50 ml) with a mixture of pyridine and (−), α-phenethylamine. The mixture of diastereoisomeric amides (7.4 g) was isolated by washing of the solvent layer with dilute HCl and water and evaporation of the solvent. The respective amide diastereoisomers were separated by liquid chromatography on a silica gel column using n-hexane/ethyl acetate (92/8%) as the eluent, to yield the resolved diastereoisomeric amides as crystalline solids designated as "A" and "B". A had $[\alpha]_D^{23} = +37.84°$ (EtOH), B had $[\alpha]_D^{23} = -49.56°$ (EtOH). Yield of A was 2.87 g, m.p. 76° C.; B was 1.94 g, m.p., 101° C. IR, mass spectra and NMR of A and B were consistent with the amide structure.

(b) Hydrolysis of diastereoisomeric amides

The resolved diastereoisomeric amide A (2.47 g) was added to a solution of dinitrogen tetroxide ($N_2O_4$) 0.15 M in $CCl_4$ (230 ml) cooled in dry ice. The slurried reaction mixture was reacted for 72 h. The reaction mixture was then quenched with ice cold ether (115 ml) and extracted with $NaHCO_3$ (5%) and water. The aqueous extract was acidified and extracted with ether. The ether was evaporated and the residual oil of the nitrosoamide (3.01 g) refluxed in $CCl_4$ (50 ml) for 20 hours. The $CCl_4$ was then evaporated and the oil reacted for 15 hours with NaOH/methanol (10 ml, 5%) to hydrolyse α-phenethyl carbinol ester formed partially in the reaction mixture. The phenethyl carbinol was extracted from the sodium salt of the resolved acid. The acid recrystallised from ethanol to give 0.85 g of the S(+) enantiomer $[\alpha]_D^{22} = +92.85°$ (EtOH) of the 1-(4-ethoxyphenyl)-2,2,3,3-tetrafluorocyclobutanecarboxylic acid m.p. 83°–4° C. In a similar experiment the amide B (1.93 g) was converted to the R(−) enantiomer $[\alpha]_D^{20} = -94.24°$ (EtOH); m.p. 82°–3° C.; yield 0.36 g.

EXAMPLE 3

(a) R(−);(±) Diastereoisomer of α-cyano-3′-phenoxybenzyl-1-(4-ethoxyphenyl)-2,2,3,3-tetrafluorocyclobutane carboxylate The R(−) 1-(4-ethoxyphenyl)-2,2,3,3-tetrafluorocyclobutane carboxylic acid obtained in Example 2 (1.02 g) was stirred with freshly distilled oxalyl chloride and heated on a steam bath. After a slow evolution of HCl ceased (1 h) the solution was cooled to room temperature. Benzene (1 ml) containing a drop of pyridine was added and evolution of gas ($CO,CO_2$) commenced again. The solution was heated on steam bath carefully to prevent violent gas evolution. In 10 minutes the gas evolution ceased. The solvents were evaporated and the acyl chloride dissolved in benzene (5 ml) was added to α-cyano-3-phenoxybenzyl carbinol in benzene containing pyridine (0.42 g). The reaction mixture was stirred at room temperature for 48 hours then the solvent layer was washed sequentially with dilute HCl, water, $NaHCO_3$, water and finally dried over anhydrous $MgSO_4$. The oil obtained after evaporation of the solvent was chromatographed on silica gel using petroleum ether (60°–80° C.): ethyl acetate as eluents. The two major peaks were separated together to yield 1.7 g of the R(−);(±) diastereoisomer of the title ester as a colourless oil; $[\alpha]_D^{20} = -20.1°$ (EtOH).

(b) Separation of R(−);(±) and R(−);(−) Diastereoisomers of α-cyano-3′-phenoxybenzyl 1-(4-ethoxyphenyl)-2,2,3,3-tetrafluorocyclobutane carboxylate 0.9 g of the purified R(−);(±) ester was separated by preparative high pressure liquid chromatography (HPLC) to yield 0.30 g of the R(−);(−) diastereoisomer ($[\alpha]_D^{20} = -38.8°$ [EtOH]) and 0.31 g of the (R−);(+) diastereoisomer ($[\alpha]_D^{20} = -3.65°$ [EtOH]) together with an unresolved intermediate fraction.

EXAMPLE 4

(a) R(−);(±) Diastereoisomer of
α-ethynyl-3′-phenoxybenzyl-1-(4-ethoxyphenyl)-
2,2,3,3-tetrafluorocyclobutane carboxylate The title compound was prepared from 1.1 g of the R(−) 1-(4-ethoxyphenyl)-2,2,3,3-tetrafluorocyclobutane carboxylic acid and 3-phenoxy-α-ethynylbenzyl carbinol using the method of Example 3(a). Yield of the product was 1.2 g with $[\alpha]_D^{20} = -21.9°$ (EtOH).

(b) Separation of R(−);(+) and R(−);(−)
Diastereoisomers of α-ethynyl-3′-phenoxybenzyl
1-(4-ethoxyphenyl)-2,2,3,3-tetrafluorocyclobutane
carboxylate 0.61 g of the purified R(−);(±) ester was separated by preparative high pressure liquid chromatography (HPLC) to yield 0.27 g of the R(−);(−) diastereoisomer ($[\alpha]_D^{20} = -34.7°$ [EtOH]) and 0.28 g of the R(−);(+) diastereoisomer ($[\alpha]_D^{20} = -9.64°$ [EtOH]) together with an unresolved intermediate fraction.

EXAMPLE 5

R(−)
1-(4-chlorophenyl)-2,2,3,3-tetrafluorocyclobutane
carboxylic acid

The racemic 1-(4-chlorophenyl)-2,2,3,3-tetrafluorocyclobutane carboxylic acid was prepared from ethyl-p-chlorophenylacetate using the method of Example 1. m.p. 112°–119° C.

The racemic acid was resolved into its R(−) and S(+) isomers using the method of Example 2.

R(−) isomer $[\alpha]_D^{20} = -107°$. (EtOH)

EXAMPLE 6

Separation of (+) and (−) stereoisomers of
α-ethynyl-3-phenoxybenzyl alcohol (−)-N-α-phenylethylphthalamic acid was prepared from phthalic anhydride and (−)α-phenylethylamine by the method of Mann and Wastom (J. Chem. Soc., 1947, 510). The ester of this phthalamic acid with racemic α-ethynyl-3-phenoxybenzyl alcohol was prepared by the method of Human and Mills (J. Chem. Soc., 1949, S77). The individual (−)(+) and (−)(−) ester diastereoisomers were separated by chromatography (HPLC) and then hydrolysed with a slight excess of alkali to recover the resolved α-ethynyl-3′-phenoxybenzyl alcohol.

(−) isomer $[\alpha]_D^{20} = -19.0°$ (EtOH)
(+) isomer $[\alpha]_D^{20} = 19.5°$ (EtOH)

EXAMPLE 7

R(−)(−) Diastereoisomer of
α-ethynyl-3′-phenoxybenzyl-1-(4-chlorophenyl)-
2,2,3,3-tetrafluorocyclobutane carboxylate R(−) 1-(4-chlorophenyl)-2,2,3,3-tetrafluorocyclobutane carboxylic acid (1.0 g, 3.54 mM) prepared as in Example 5, was refluxed with thionyl chloride (1.5 g) for 45 minutes then excess thionyl chloride was removed in vacuo. The residual acyl chloride was dissolved in petroleum ether 40°–60° (30 ml) and added over 10 minutes to a stirred mixture of (−)α-ethynyl-3-phenoxybenzyl alcohol (0.87 g, 3.88 mM), pyridine (0.4 g, 5 mM) benzene (40 ml) and petroleum ether 40°–60° (30 ml) maintained at 15° C. The mixture was stirred an additional 4 hours then washed with ice water, sodium bicarbonate solution, dried over sodium sulphate and solvent removed in vacuo. The residue was chromatographed over silica gel eluting with benzene/petroleum ether (40°–60°) 1:2 to yield the ester as a colourless oil 1.47 g 85%. Rotation $[\alpha]_D^{20} = -37.6°$ (EtOH).

EXAMPLE 8

(R(−)(±) diastereoisomer of
α-ethynyl-3′-phenoxybenzyl-1-(4-chlorophenyl)-
2,2,3,3-tetrafluorocyclobutane carboxylate The R(−)(+) diastereoisomer of α-ethynyl-3′-phenoxybenzyl-1-(4-chlorophenyl)-2,2,3,3-tetrafluorocyclobutane carboxylate was prepared by esterifying R(−)1-(4-chlorophenyl)-2,2,3,3-tetrafluorocyclobutane carboxylic acid (prepared as in Example 5) with (+)α-ethyl-3′-phenoxybenzyl alcohol (prepared in Example 6) using the method of Example 7.

The title R(−)(±) diastereoisomer was prepared by mixing equal quantities of the R(−)(−) diastereoisomer prepared in Example 7 and the R(−)(+) diastereoisomer prepared above.

EXAMPLE 9

R(−)(−) diastereoisomer of
α-ethynyl-3′-phenoxybenzyl
1-(3,4-methylenedioxyphenyl)-2,2,3,3-tetrafluorocyclobutane carboxylate The R(−) isomer of 1-(3,4-methylenedioxyphenyl)-2,2,3,3-tetrafluorocyclobutane carboxylic acid was prepared using the methods of Examples 1 and 2. It was then esterified with the (−) isomer of α-ethynyl-3-phenoxybenzyl alcohol using the method of Example 7.

The title compound had optical rotation $[\alpha]_D^{20} = -59.4°$.

EXAMPLE 10

Insecticidal Activity

Insecticidal activity was investigated against blowfly, *Lucilia cuprina*. The method used was as follows:

(a) The compounds were tested for activity against a dieldrin susceptible strain (LBB) which had been collected before dieldrin usage in the field.

The test compound was applied in acetone solution, 0.5 μl dispensed with a Drummond micropipette to the dorsum of the thorax of 2–3 day old females. Adult flies were fed on water and sugar-only and maintained at 25° C. and 60–70% RH. The mortalities were determined after 24 hours. Moribund flies were regarded as dead. The $LD_{50}$ values, in terms of concentration, were interpolated from a probit/log dose graph using a computer program.

(b) Potentiation

The compound was also tested on the insects described above in conjunction with the potentiator piperonyl butoxide by pretreating each insect with 1 μl of a 2% solution of the potentiator in acetone.

The mortalities were counted at 48 hours after treatment and compared with acetone and acetone/potentiator controls.

The $LD_{50}$ value was determined as described above.

About the same levels of potentiation were obtained when piperonyl butoxide was replaced by an equal amount of 'Sesoxane'.

Using the above-described techniques, $LD_{50}$ values were determined on each of the diastereoisomers listed in Table 1.

Comparative tests were also carried out on two commercially available, synthetic pyrethroid insecticides, namely "Permethrin", i.e., the 3'-phenoxybenzyl ester of 3-(2',2'-dichlorovinyl)-2,2-dimethylcyclopropane carboxylic acid;

and

"Decamethrin", i.e. the (IR)(3R)cis-form of α-cyano-3'-phenoxybenzyl ester of 3-(2',2'-dibromovinyl)-2,2-dimethylcyclopropane carboxylic acid.

For ease of comparison the results obtained are expressed in Table 1, in terms of a "potency index" given by $$\text{Potency Index} = \frac{\text{LD}_{50} \text{ for Permethrin}}{\text{LD}_{50} \text{ for test compound}} \times \frac{100}{1}$$

The $LD_{50}$ for permethrin was determined concurrently with the $LD_{50}$ for the test compound.

The configurations of the compounds as stated were assigned on the basis of the measured optical rotations. Absolute configurations where quoted are based on the configuration of a related enantiomer determined by x-ray crystallographic analysis.

TABLE 1

Comparison of Insecticidal Activity of Enantiomers against *Lucilia Cuprina*

| Configuration of Compound | | Potency Index Compound | |
|---|---|---|---|
| Acid moiety | Alcohol moiety | alone | With synergist |
| α-ethynyl-3'-phenoxybenzyl 1-(4-ethoxyphenyl)2,2,3,3-tetrafluorocyclobutane-1-carboxylate | | | |
| (±) | (±) | 170 | 360 |
| R(−) | (±) | 320 | 350 |
| R(−) | (−) | 1200 | 4000 |
| R(−) | (+) | 36 | 42 |
| α-cyano-3'-phenoxybenzyl 1-(4-ethoxyphenyl)-2,2,3,3-tetrafluorocyclobutane-1-carboxylate | | | |
| (±) | (±) | 80 | 1000 |
| R(−) | (±) | 112 | 2200 |
| R(−) | (−) | 307 | 20000 |
| R(−) | (+) | 21 | 100 |
| S(+) | (±) | 8 | 22 |
| S(+) | (+) | 19 | 33 |
| S(+) | (−) | 0.6 | 3 |
| Permethrin | | 100 | 100 |
| Decamethrin | | 330 | 2000 |
| α-ethynyl-3'-phenoxybenzyl 1-(4-chlorophenyl)2,2,3,3-tetrafluorocyclobutane-1-carboxylate | | | |
| (±) | (±) | 250 | 100 |
| R(−) | (±) | 650 | 170 |
| R(−) | (−) | 1200 | 670 |
| α-ethynyl-3'-phenoxybenzyl 1-(3,4-methylenedioxyphenyl)2,2,3,3-tetrafluorocyclobutane-1-carboxylate | | | |
| (±) | (±) | 260 | 280 |
| R(−) | (−) | 830 | 500 |

We claim:

1. Compounds of the formula Ia

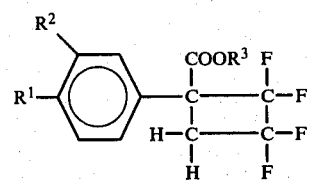

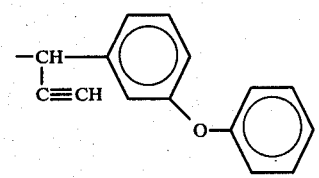

characterised in that $R^1$ is ethoxy or chloro, and $R^2$ is hydrogen;

$R^3$ is and the compounds are in the form of the (−)(−) diastereoisomers.

2. (−)(−)-α-ethynyl-3'-phenoxybenzyl 1-(4-ethoxyphenyl)-2,2,3,3-tetrafluorocyclobutane carboxylate.

3. (−)(−)-α-ethynyl-3'-phenoxybenzyl 1-(4-chlorophenyl)-2,2,3,3-tetrafluorocyclobutane carboxylate.

4. Insecticidal compositions, characterised in that they comprise an insecticidally effective amount of one or more of the compounds stated in claim 1, incorporated in a suitable inert liquid or solid carrier.

5. Insecticidal compositions as claimed in claim 4, characterised in that they additionally contain at least one synergistic or potentiating agent of the class of microsomal oxidase inhibitors which is a pyrethrin synergist.

6. Insecticidal compositions as claimed in claim 5, characterised in that the synergist is one of the following:

α[2-(2-butoxyethoxy)ethoxy]-4,5-methylenedioxy-2-propyltoluene;

3-hexyl-5(3,4-methylenedioxyphenyl)-2-cyclohexanone;

2-(3,4-methylenedioxy-phenoxy)-3,6,9-trioxaundecane;

1,2-(methylenedioxy)-4-[2-octylsulfinyl)propyl]-benzene;

dipropyl-5,6,7,8-tetrahydro-7-methylnaphtho-[2,3-d]-1,3-dioxole-5,6-dicarboxylate.

7. Insecticidal compositions as claimed in claim 5, characterised in that the synergist is used in an amount from about 1/1000th to 5 times the weight of the compound I.

8. Insecticidal compositions as claimed in claim 5, characterised in that the synthergist is used in an amount from about 1/100th to an equal part by weight per part of the compound I.

9. A method of combatting insect pests, characterised in that an insecticidally effective amount of a compound or composition as claimed in any one of claims 1 to 3 or 4 to 8, is applied to the insects and/or their locus.

* * * * *